United States Patent [19]

Farquhar et al.

[11] Patent Number: 5,196,522
[45] Date of Patent: Mar. 23, 1993

[54] ANTHRACYCLINE ANALOGUES BEARING LATENT ALKYLATING SUBSTITUENTS

[75] Inventors: David Farquhar; Abdallah Cherif, both of Houston, Tex.

[73] Assignee: Board of Regents, The University of Texas System, Austin, Tex.

[21] Appl. No.: 608,149

[22] Filed: Nov. 1, 1990

[51] Int. Cl.⁵ .......................................... C07H 15/24
[52] U.S. Cl. .................................................. 536/6.4
[58] Field of Search ............................ 536/6.4; 514/34

[56] References Cited

U.S. PATENT DOCUMENTS

| | | | |
|---|---|---|---|
| 4,035,566 | 7/1977 | Israel et al. | 536/6.4 |
| 4,109,076 | 8/1978 | Henry et al. | 536/6.4 |
| 4,301,277 | 11/1981 | Acton et al. | 536/6.4 |
| 4,464,529 | 8/1984 | Mosher et al. | 536/6.4 |
| 4,585,859 | 4/1986 | Mosher et al. | 536/6.4 |
| 4,755,619 | 7/1988 | Creighton et al. | 560/169 |
| 4,826,964 | 5/1989 | Acton et al. | 536/6.4 |
| 4,841,085 | 6/1989 | Farquhar et al. | 538/180 |
| 4,950,738 | 8/1990 | King et al. | 536/6.4 |

OTHER PUBLICATIONS

Tsuchiya, T. et al., Synthesis and Antitumor Activities of 14-O-Acyl Derivatives of 7-O-(2,6-Dideoxy-2-Fluoro-α-L-Talopyrangosyl) Adriamycinone, *J. of Antibiotics* (1988) XLI:988–991.

Griffith, W. P. et al., Preparation and Use of Tetra-n-butylammonium Perruthenate (TBAP Reagent) and Tetra-n-propylammonium Per-ruthenate (TPAP Reagent) as New Catalytic Oxidants for Alcohols, *The Journal Chem. Soc., Chem. Commun.*, (9187) 1625–1627.

Acton, E. M. et al., N-(2-Hydroxyethyl)doxorubicin from Hydrolysis of 3'-Deamino-3'-(3-cyano-4-morpholinyl)doxorubicin, *J. Med. Chem.* (1986) 29:2120–2122.

Streeter, D. G. et al., Uptake and Retention of Morpholinyl Anthracyclines by Adriamycin-Sensitive and -Resistant P388 Cells, *Cancer Chemother. Pharmacol.*, (1986) 16:247–252.

Sikic, B. I. et al., Dissociation of Antitumor Potency from Anthracycline Cardiotoxicity in a Doxorubicin Analog, *Science* (1985) 328:1544–1546.

(List continued on next page.)

*Primary Examiner*—Johnnie R. Brown
*Assistant Examiner*—Elli Peselev
*Attorney, Agent, or Firm*—Arnold, White & Durkee

[57] ABSTRACT

The present invention is a compound having the structure

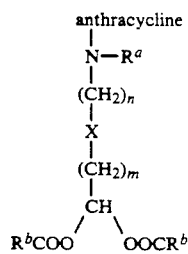

where:
anthracycline is doxorubicin, daunorubicin or a derivative thereof;
N is the 3' nitrogen of daunssamine;
$R^a$ is H or alkyl;
X is, O, S, $CR^c_2$ or $NR^2$ where $R^c$ is H or alkyl; $R^b$ is alkyl or aryl; n is 1 to 6; and m is 0 to 6.

$R^a$ and $R^c$ are preferably H, methyl, ethyl, propyl or butyl, although other alkyl substituents are usable. $R^b$ is alkyl or aryl. The compound of the present invention as described above is activatable in vivo by esterases and spontaneous dehydration to form an aldehyde. The aldehyde may couple to nucleophiles of intracellular macromolecules. The compounds of the present invention are cytotoxically effective in the inhibition of human myeloma cells.

18 Claims, 2 Drawing Sheets

OTHER PUBLICATIONS

Streeter, D. G. et al., Comparative Cytotoxicities of Various Morpholinyl Anthracyclines, *Cancer Chemother. Pharmacol.* (1985) 14:160–164.

Arcamone, F., Properties of Antitumor Anthracyclines and New Developments in Their Application: Cain Memorial Award Lecture, *Cancer Research* (1985) 45:5995–5999.

Acton, E. M. et al., Intensely Potent Morpholinyl Anthracyclines, *J. Med. Chem.* (1984) 27:638–645.

Horton, D. et al., 14-Esters of 7-O-(3,4-Di--O-Acetyl-2,6-Dideoxy-60 -L-Lyo-Hexopyranosyl-)adriamycinone: Synthesis and Antitumor Activity, *J. of Antibiotics* (1983) XXXVI:1211–1215.

Johnston, J. B. et al., 3'-(3-Cyano-4-Morpholinyl)-3-'-Deaminoadriamycin: A New Anthracycline With Intense Potency, *Biochemical Pharmacology* (1983) 32:3255–3258.

Acton, E. M. et al., Synthesis and Preliminary Antitumor Evaluation of 5-Iminodoxorubicin, *J. Med. Chem.* (1981) 24:669–673.

Tong, G. L. et al., Adriamycin Analogues. 3. Synthesis of N-Alkylated Anthracyclines With Enhanced Efficacy and Reduced Cardiotoxicity, *J. Med. Chem.* (1979) 22:912–918.

Corey, E. J. et al., Pyridinium Chlorochromate. An Efficient Reagent for Oxidation of Primary and Secondary Alcohols to Carbonyl Compounds, *Tetrahedron Letters* (1975) 31:2647–2650.

Fieser, L. F. et al., *Reagents for Organic Synthesis* (1967) 1:142–144.

Arcamone, F., *Doxorubicin Anticancer Antibiotics*, Academic press, (1981) 194–258.

Wang, Y. and Farquhar, D., Aldophosphamide Acetal Diacetate and Structural Analogues: Synthesis and Cytotoxicity Studies, *J. Med. Chem.* (1991) 34:197–203.

Acton, E. M. et al., Morpholinyl Anthracyclines in: *Anthracycline and Anthracenedione-Based Anticancer Agents*, William J. Lown; Ed., Elsevier Science Publishers: Amsterdam (1988) 55–101.

Muggia, F. M. et al., *Anthracycline Antibiotics in Cancer Therapy*, Martinus Nijhoff Publishers, 91982) 175–219.

Search of Dialog Information Services files 265, 399, 155, 350, 351, 340, 72 and 159.

ANTHRACYCLINE ANALOGUES BEARING LATENT ALKYLATING SUBSTITUENTS

Work relating to the development of the present invention was supported by Grant CA 42708 from the National Institutes of Health, DHHS. This support gives the United States Government certain rights in the present invention.

BACKGROUND OF THE INVENTION

This invention is in the field of anthracycline chemistry. More particularly it concerns derivatives of the anthracyclines, doxorubicin and daunorubicin, that are useful as antitumor agents.

Daunorubicin is used for the treatment of certain leukemias. Doxorubicin (adriamycin) is one of the most useful anticancer drugs in use at this time. Doxorubicin is a principle agent in the treatment of an unusually wide number of solid tumors and leukemias. Regrettably, many patients with these tumors fail to respond and essentially no patients with certain serious tumor types (colon cancer, melanoma) are successfully treated. Additionally, in some patients chronic adriamycin treatment produces irreversible heart damage that can be fatal if continued. Thus, there is great need for analogues which give a better rate of response, a wider spectrum of response, and/or reduced cardiotoxicity. More effective and less toxic agents are widely sought and are a fundamental object of this invention.

Much of the history and prior art of doxorubicin and its anthracycline analogues is found in the article "Adriamycin" by David W. Henry, "ACS Symposium Series, NO. 30, *Cancer Chemotherapy, American Chemical Society*, pp. 15–57 (1976) and in the book *Doxorubicin* by Frederico Arcamone, Academic Press, 1981. The derivative AD32 is disclosed in U.S. Pat. No. 4,035,566, dated Jul. 12, 1977.

5-Iminodaunorubicin is shown in U.S. Pat. No. 4,109,076 which issued on Aug. 22, 1978, to David W. Henry and George L. Tong. The doxorubicin equivalent is shown in "Synthesis and Preliminary Antitumor Evaluation of 5-Iminodoxorubicin", *J. Med. Chem.* 24, 669 (1981) by Edward M. Acton and George L. Tong. 5-Iminodaunorubicin retained activity with reduced side effects with 5-Iminodoxorubicin showed enhanced activity but required higher dosages.

3'-Deamino-3-(4-morpholinyl)daunorubicin is described in U.S. Pat. No. 4,301,277 issued on Nov. 17, 1981 to Acton et al. It was active at one-fortieth the dose of doxorubicin but gave a substantially identical T/C value (166% vs 160% against P388). This compound and its preparation and properties are also disclosed in "Enhanced Antitumor Properties of 3'-(4-Morpholinyl) and 3'-(4-Methoxy-1-piperidinyl) Derivatives of 3'-Deaminodaunorubicin", *J. Med. Chem.*, 25, pp. 18–24 (1982) by Mosher et al.

A general reductive alkylation process for preparing certain new semi-synthetic anthracycline derivatives is described in "Adriamycin Analogues. 3. Synthesis of N-Alkylated Anthracyclines With Enhanced Efficacy and Reduced Cardiotoxicity", *J. Med. Chem.*, 22 pp. 912–918 (1979) by Tong et al.

A group of daunorubicin and doxorubicin derivatives is disclosed in U.S. Pat. No. 4,585,859, issued Apr. 29, 1986. Included in this group are 3'-deamino-3'-(3"-cyano-4"-morpholinyl doxorubicin; 3'-deamino-3'(3"-cyano-4"-morpholinyl)-13-dihydrodoxorubicin; (3'-deamino-3'-(3"-cyano-4"-morpholinyl)-3-dihydrodaunorubicin; and 3'-deamino-3'-(4"-morpholinyl-5-iminodoxorubicin and derivatives thereof which have activity as antitumor agents.

U.S. Pat. No. 4,841,085, Jun. 20, 1989, by one of the present inventors, describes diacetatopropyl phosphoramidic mustard derivatives activatable in vivo by endogenous esterases.

U.S. Pat. No. 4,826,964 issued May 2, 1989 to Acton et al. describes cyanomorpholino doxorubicin which contains an esterified hydroxyl group on the morpholino group. There appears to be little, other than general classification, in common between this compound and those of the present invention.

U.S. Pat. No. 4,755,619 issued Jul. 5, 1988 to Creighton et al. discusses a multifunctional compound which is a derivatized dicarbonylalkyl N-substituted drug which may be activated in vivo by hydrolysis of an ester group. This is indirectly related to the compound of the present invention but is chemically quite different. It is suggested, see column 9, lines 20–30, that the subject compounds and anthracyclines such as doxorubicin may be advantageously used together to treat cancer synergistically while avoiding the cardiotoxicity of the doxorubicin. While there was some analogy in chemical structure and in vivo activation, this reference does not seriously detract from the patentability of the present invention.

The Tsuchiya et al. reference (J. Antibiotics, Jul. 1988, 988–991) describe doxorubicin derivatives with excellent activities against L1210 leukemia and lowered toxicities as compared to doxorubicin. These derivatives, although having ester linkages, are nonanalogous to those of the present invention.

The Acton et al. reference (J. Med. Chem. 1986, 29, 2120–2122) describes cyanomorpholinyl doxorubicin compounds and their properties.

The Horton and Priebe reference (J. Antibiotics, XXXVI, 1211–1215, 1983) describes a range of esterified anthracycline derivatives. None of these derivatives has the bis-acetal substituents of the present invention.

The Tong et al. reference (J. Med. Chem. 8, 912–918, 1979) describes various N-alkyl and N,N-dialkyl anthracyclines and their 13-dihydro derivatives.

The pertinent subject matter of the above references is specifically incorporated herein by reference.

SUMMARY OF THE INVENTION

The present invention is a compound having the structure

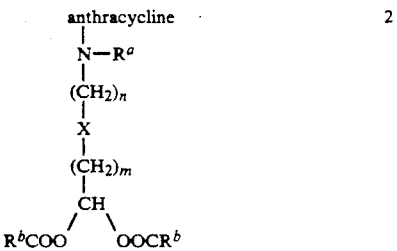

where:
anthracycline is doxorubicin, daunorubicin or a derivative thereof;
N is the 3' nitrogen of daunosamine;
$R^a$ is H or alkyl;

X is O or S, $CR^c_2$ or $NR^c$, where $R^c$ is H or alkyl;
$R^b$ is alkyl or aryl;
n is 1 to 6; and
m is 0 to 6.

$R^a$ and $R^c$ are preferably and independently H, methyl, ethyl, propyl or butyl. $R^b$ when an alkyl is preferably methyl, ethyl, propyl or butyl, although other alkyl substituents are usable. The compound of the present invention as described above is activatable in vivo by esterases and spontaneous dehydration to form an aldehyde. The aldehyde may couple to nucleophiles of intracellular macromolecules. The compounds of the present invention are cytotoxically effective in the inhibition of human leukemia myeloma cells.

DESCRIPTION OF PREFERRED EMBODIMENT

The anthracycline antibiotic doxorubicin is effective in the palliative management of a wide variety of human malignancies[1]. However, the clinical utility of doxorubicin is limited by a number of problems, including intrinsic and acquired drug resistance and dose-dependent cardiomyopathy. Numerous analogues have been synthesized in an attempt to overcome these shortcomings [2-4] A series of derivatives in which the 3'-amino group of the daunosamine sugar is replaced with a morpholino substituent has been reported by Acton and coworkers. [5-7] One of these analogues, 3'-deamino-3'-(3-cyano-4-morpholinyl)-adriamycin (MRA-CN) is 100 to 1000 times more cytotoxic than doxorubicin in vitro[7-10] and in vivo[6,11] and retains its potency against several tumor cell lines with acquired resistance to doxorubicin.[9,12,13]

The compounds of the present invention, bis(acyloxy) acetals of an anthracycline such as doxorubicin (adriamycin), for example, are designed to be relatively stable, non-toxic but subject to activation by in vivo enzymes (esterases) to form an aldehyde hydrate from the bis (acyloxy) acetal. This aldehyde hydrate is labile and eliminates water to form an aldehyde. By varying the composition of the anthracycline bisacyloxy-bearing side chain, many different analogues are possible, all of which will be activatable at various rates by endogenous esterases and spontaneous decompositions to form active anthracycline aldehyde derivatives. It is possible to vary the composition of the side chain in both composition and length to prepare a series of such analogues having desired specificities and/or non-toxicities toward particular biological sites. The side chain connecting the anthracycline and the bis acyloxy substituent will comprise at least one methylene ($CH_2$) group and may contain up to 9 such groups. When more than one methylene group is present there may be an additional spacer group such as O, S or $NR^a$ where $R^a$ is H or alkyl with usually less than 5 carbon atoms, depending upon the particular properties desired.

Figure 1:
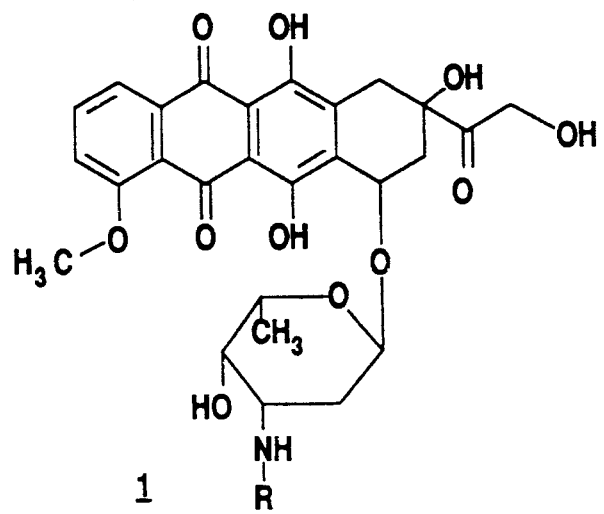
FIG. 1 schematically describes potentially alkylating derivatives of doxorubicin (a, R $=NHCOC_6H_4$(p-)$SO_2F$; b, R $=NHCOCH_2Cl$; d, R $=NHCON(NO)CH_2CH_2Cl$).

A series of analogues, 1, (FIG. 1) bearing alkylating or latent alkylating substituents, R, on the 3'-position of the daunosamine sugar were prepared. These compounds were designed on the premise that alkylating anthracyclines should bind covalently to critical intracellular macromolecules and overcome resistance to doxorubicin arising from reduced cellular drug accumulation. However, in growth inhibitory studies against mouse (L1210 and P388) and human (uterine sarcoma, myelocytic) tumor cells in vitro, these analogues were 5- to 100-fold less potent than the parent compound (doxorubicin). These analogs nevertheless did retain their cytotoxic activity against variants of these same cell lines which were resistant to doxorubicin.

To identify new alkylating anthracyclines with increased potency, a series of doxorubicin analogues was synthesized in which the 3'-amino group is substituted with a latent alkanal or heteroalkanal group. A rationale for the design of these compounds was that: (a) the latent alkanal or heteroalkanal groups would be converted to the corresponding free aldehydes when the drugs were placed in a biological medium (such as cells or whole organisms), and (b) the liberated free aldehydes would react with nucleophiles (such as amino or sulfhydryl groups) proximate to the DNA drug-binding site to form covalent adducts. As a consequence, drug egress from the cell should be inhibited.

Because of the intrinsic chemical reactivity of free aldehydes, the alkanal (or heteroalkanal) groups were introduced into the doxorubicin molecule in latentiated form. Bis(acyloxy) groups were selected for this purpose. The general structure of the new doxorubicin analogues is shown in FIG. 2, where the anthracycline is doxorubicin or daunorubicin.

Additionally, the acyloxy group may be varied. For example, the acyloxy group may be acetate, propionate, butyrate (n or t) or even benzoate or substituted benzoate. The acyloxy substituent may also be varied to control the rate of drug activation resulting from ester hydrolysis. For example, certain sterically hindered ester groups may be hydrolyzed much less rapidly than a simpler substituent such as acetoxy.

Figure 2:
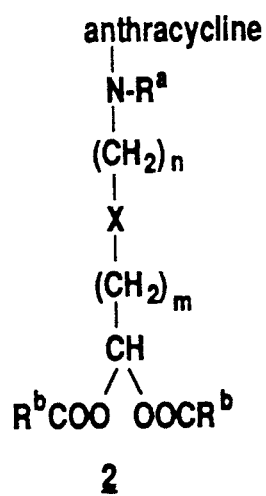
FIG. 2 schematically describes preferred compounds of the present invention (anthracycline is doxorubicin, daunorubicin or a derivative thereof; N is the 3' nitrogen of daunosamine; $R^a$ is H or alkyl; X is O, S, $CR^c_2$ or $NR^c$ where $R^c$ is H or alkyl; $R^b$ is alkyl or aryl; n is 1 to 6; and m is 0 to 6.
Figure 3:
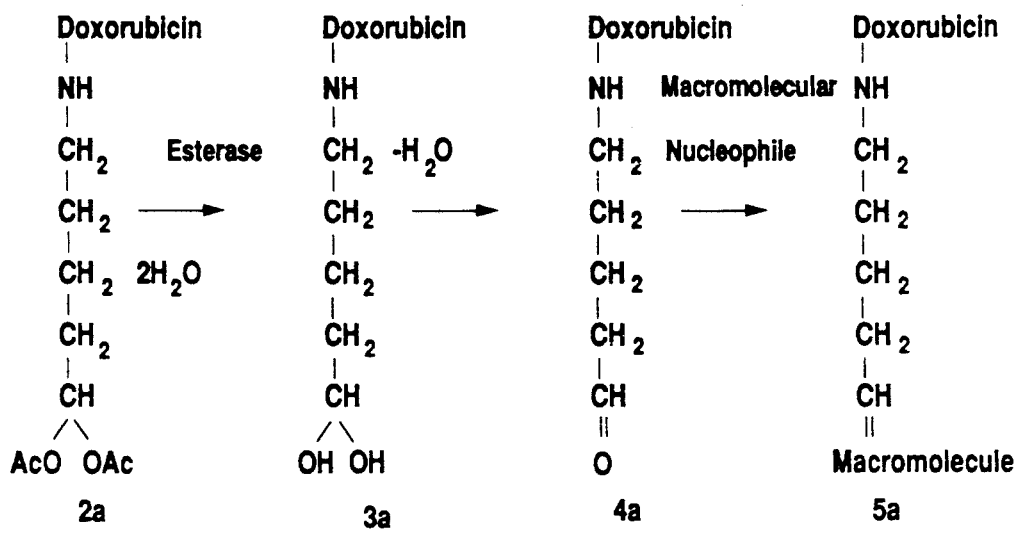
FIG. 3 schematically describes the activation mechanism for the compounds of the present invention where Doxorubicin is the $N^{3'}$-substituted doxorubicin residue, and Macromolecule represents a cellular marcolmolecule.

The mechanism for regeneration of the free aldehyde is illustrated in FIG. 3 with respect to compound 2a (FIG. 2 n =2, m =1, X =$CR^3_2$ where $R^c$ is H, $R^b$ =$CH_3$ and $R^a$=H). In the presence of carboxylate esterases, enzymes that are ubiquitous in tissue, and which show low substrate specificity, compound 2a can be hydrolyzed to the corresponding aldehyde hydrate, 3a. Elimination of water from 3a generates the free aldehyde, 4a. The aldehyde group can then react with a nucleophile such as one on a macromolecule proximate to, or within, a DNA-binding site to form a potential covalent drug-DNA adduct, 5a.

Apart from recent studies by the inventors' laboratory with cyclophosphamide metabolites (see U.S. Pat. No. 4,841,085 and Aldophosphamide bis(acetoxy)acetal and Structural Analogues. J. Med. Chem., In Press, 1990, for example) this approach to the bioreversible latentiation of aldehydes has not been described previously and has not at all been described before for anthracycline derivatives.

An important aspect of this strategy is that by judicious selection of the acyloxy groups, it should be possible to modify the lipophilicity and aqueous solubility of these analogues. Moreover, since these compounds are designed to be activated by carboxylate esterases (enzymes present in all cells), the acyloxy masking groups can be altered to control the rate at which the active "alkylating" anthracyclines are formed.

Figure 4:
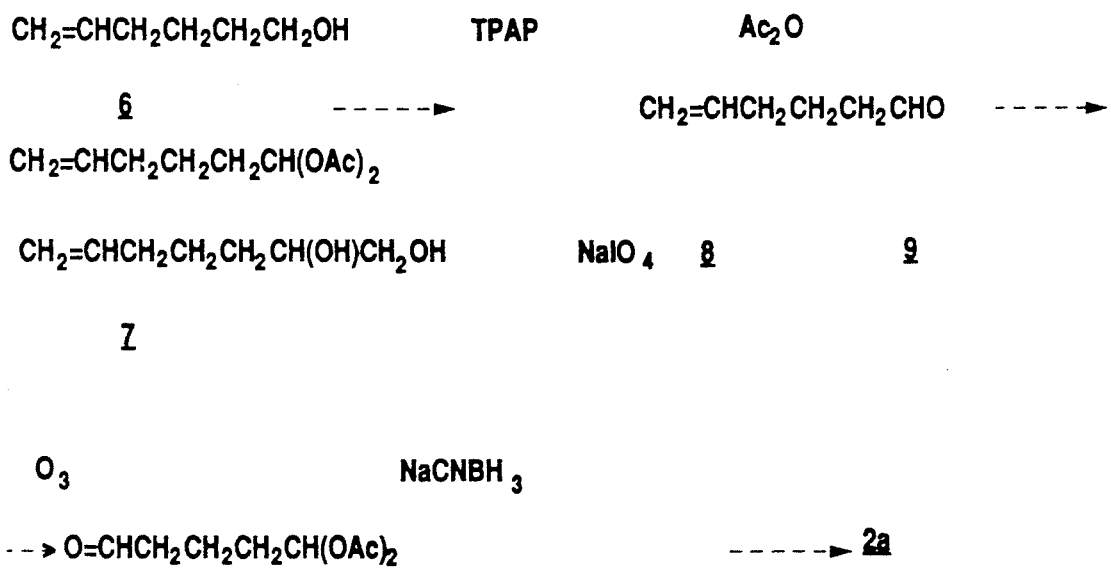
FIG. 4 generically describes a synthetic scheme for an embodiment of the present invention.

A number of compounds having the general structure 2 have been prepared. These were synthesized by condensing doxorubicin with a dialdehyde monoacetal then reducing the intermediate imine with NaBH$_3$CN. The overall synthetic strategy can be exemplified with respect to 2a as schematically illustrated in FIG. 4.

To the best of applicants' knowledge, dialdehyde monoacetals such as 10 have not been reported previously. [These should be versatile synthetons in organic synthesis since the acetal ester groups can be cleaved under extremely mild conditions (weak base or esterase activity)]. Condensation of 10 with doxorubicin, 11, in the presence of NaCNBH$_3$ generated 2a directly in >50% yield. Evidence for the structure of 2a was obtained by $^1$H and COSY NMR, and by mass spectrometry. The compound is freely soluble in aqueous media and is stable at neutral pH.

To investigate structure-activity relationships for this class of compounds, the analogs (based upon structure 2 of FIG. 2) shown in Table 1 have been prepared.

TABLE 1

| | | | | | |
|---|---|---|---|---|---|
| 2a | n = 2, | m = 1, | X = CH$_2$, | R$^b$ = CH$_3$, | R$^a$ = H |
| 2b | n = 2, | m = 1, | X = O, | R$^b$ = CH$_3$, | R$^a$ = CH$_3$ |
| 2c | n = 2, | m = 0, | X = CH$_2$, | R$^b$ = CH$_3$, | R$^a$ = H |
| 2d | n = 2, | m = 2, | X = CH$_2$, | R$^b$ = CH$_3$, | R$^a$ = H |
| 2e | n = 2, | m = 0, | X = C(CH$_3$)$_2$, | R$^b$ = CH$_3$, | R$^a$ = H |
| 2f | n = 2, | m = 2, | X = O, | R$^b$ = CH$_3$, | R$^a$ = H |
| 2g | n = 2 | m = 4, | X = CH$_2$, | R$^b$ = CH$_3$, | R$^a$ = H |

This strategy obviously may be readily extended to the synthesis of a series of analogues where, e.g., X = O, S, NR$^{c\,l\,or\,CRc}$_2 where R$^c$ is H or alkyl; n = 1-6; m = 0-6; R$^a$ = H, CH$_3$, C$_2$H$_5$, C$_3$H$_7$ or other hydrocarbons (C$_x$H$_{x+1}$); and R$^b$ = CH$_3$, C$_2$H$_5$, C$_3$H$_7$, or C(CH$_3$)$_3$. While hydrochloride salts have been prepared, it is well known to utilize other pharmaceutically acceptable acids in place of hydrochloric acid to make numerous pharmaceutically acceptable salts.

EXAMPLE 1
Cytotoxicity Studies

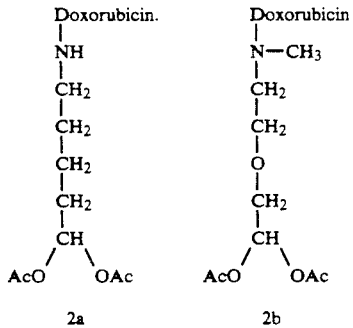

TABLE 2

| Compound index | CEM$^b$ cells | IC$_{50}{}^a$ (nM) CEM(VLB)$^c$ cells | Resistance ([CEM(VLB)]/[CEM]) |
|---|---|---|---|
| Doxorubicin | 10 | 1340 | 134 |
| Compound 2a | 0.15 | 1 | 6 |
| Compound 2b | 3 | 15 | 5 |

$^a$Determined after six days incubation with drug at 37° C.
$^b$A human T-lymphoblastic cell line
$^c$A human T-lymphoblastic cell line resistant to Velban (vinblastine)

Compound 2a was 60 times more toxic to the parent CEM cells than doxorubicin, and showed markedly reduced cross resistance against the velban resistant mutant.

In related studies compound 2a was shown to be 400 times more potent (IC$_{50}$ = 1.5 nM) to 8226R40 human myeloma cells than doxorubicin (IC$_{50}$ = 600 nM).

EXAMPLE 2
Synthetic and Related Methods

Experimental

Nuclear magnetic resonance spectra ($^1$H and $^{13}$C) were recorded at ambient temperature on an IBM-Bruker Model NR/200 AF spectrometer in the Fourier transform mode in CDCl$_3$ with tetramethylsilane as an internal reference. Chemical shifts (o) are reported in parts per million (ppm) and coupling constants (J) in hertz units. Specialist NMR techniques used for structural assignment include: off-resonance decoupling plus single frequency, selective heteronuclear decoupling, homonuclear shift-correlated 2D-NMR (COSY), homonuclear shift-correlated 2D-NMR with a delay period to emphasize long range or small coupling (COSYLR), and heteronuclear shift-correlated 2D-NMR using polarization transfer from $^1$H to $^{13}$C via Jcx (XH-CORR). Mass spectral analyses were conducted at TexMS, 15701 West Hardy Road, Houston, Tx using an atmospheric pressure desorption technique. All chemical reactions were carried out in dry glassware and were protected from atmospheric moisture. Solvents were dried over freshly activated (300° C./1 h) molecular sieves (type 4 A). Evaporations were carried out on a rotary evaporator under aspirator vacuum at a bath temperature of <25° C. The homogeneity of the products was determined by ascending TLC on silica-coated glass plates (silica gel 60 F 254, Merck) using mixtures of CHCl$_3$-MeOH as the eluting solvent. Preparative separations were performed on thick layers (20 cm ×20 cm 33 2 mm) of the same adsorbent or by column chromatography on silica gel (Merck, 230–400 mesh) using mixtures of CHCl$_3$-MeOH as eluent.

Preparation of 5-Hexen-1-al (8)

Method A

A solution of the Jones reagent[16] in acetone (10 mL, 2.67 M) was added, dropwise, with stirring over 10 min to a solution of 5-hexen-1-ol (6) (2 mL, 1.67 g, 17 mmol) in acetone (5 mL) at 0° C. The reaction mixture was maintained at 5° C. for 1 h. Saturated NaHCO$_3$ solution was added to bring the pH to 7.0 and the mixture was extracted with CHCl$_3$ (3 ×20 mL). The combined extracts were washed with H$_2$O (3 ×20 mL), and dried over anhydrous Na$_2$SO$_4$. The solvent was evaporated to give a crude product, which was then purified by filtering-column chromatography on silica gel (98:2 CHCl$_3$/MeOH) to give 0.98 g (10 mmol) of pure 5-hexen-1-al (8) as a colorless oil. Yield 59%.

$^1$H NMR [chemical shift (o), multiplicity, coupling constant (Hz), number of protons, atom]: 9.71 (t, J = 1 Hz, 1 H, H-1), 5.75 (m, 1 H, H-5), 5.04 (m, 2 H, H-6), 2.45 (m, 2 H, H-2), 2.08 (m, 2 H, H-4), 1.72 (m, 2 H, H-3).

hu 13C NMR (ppm, atom): 201.95 (C-1), 137.18 (C-5), 115.07 (C-6), 42.67 (C-2), 32.55 (C-4), 20.75 (C-3).

Method B

A solution of 5-hexen-1-ol (6) (2 mL, 1.67 g, 17 mmol) in CH$_2$Cl$_2$(5 mL) was added in one portion to a stirred solution of pyridinium chlorochromate[16] (5.5 g, 25.5 mmol) in anhydrous CH$_2$Cl$_2$ (35 mL) contained in a 100 mL round bottomed flask fitted with a reflux condenser. After 2.5 h at ambient temperature, dry ether (40 mL) was added. The organic supernatant was decanted and the residual black gum was triturated with anhydrous ether (3 ×10 mL) until a black granular solid remained. The organic extracts were combined, filtered through a short pad of florisil, then concentrated under reduced pressure. The residual liquid was passed through a short Vigreaux column to give 1.37 g of pure 5-hexen-1-al (8) (14 mmol, 82%).

The spectral properties of the compound were identical with that of the product obtained by Method A.

Method C 4A powdered molecular sieves (500 mg/mmol, 8.5 g) was added to a solution of 5-hexen-1-ol (6) (2 mL, 1.67 g, 17 mmol) and N-methylmorpholine N-oxide (1.5 eq., 25.6 mmol, 3.4 g) in CH$_2$Cl$_2$ (35 mL). The mixture was stirred for 10 min at room temperature under a nitrogen atmosphere then tetrapropyl-ammonium perruthenate (TPAP)[17] (0.30 g, 0.85 mmol, 5 mol%) was added in one portion. The initially green mixture progressively darkened. The reaction was completed after 2h at room temperature (as evidenced by TLC), CH$_2$Cl$_2$ (35 mL) was added and the mixture was passed first through a short pad of filter agent, (Celite). The filtrate was evaporated and the residual crude was purified by filtering-column chromatography on silica gel (98:2, CHCl$_3$/MeOH) to afford 1.47 g of pure 5-hexen-1-al (8) (15 mmol, 88%).

The spectral properties of the compound were identical with that of the product obtained by Method A.

Since the TPAP oxidation procedure gave the best yields and was the most convenient, it was used for all subsequent procedures for the preparation of aldehydes from the corresponding alcohols.

4-Penten-1-al (13)

This product was prepared from:

a: 4-Penten-1-ol (12) (76 mL, 1.46 g, 17 mmol) as desribed for 5-hexen-1-al (8), Method C. The total yield of the desired aldehyde (13) was 91%, (15.58 mmol, 1.31 g).

$^1$H NMR: 9.91 (t, J = 1 Hz, 1 H, H-1), 5.80 (m, 1 H, H-4), 5.21 (m, 2 H, H-5), 2.12 (m, 2 H, H-2), 1.95 (m, 2 H, H-3).

$^{13}$C NMR: 200.28 (C-1), 137.61 (C$_4$), 114.96 (C-5), 32.80 (C-2), 32.2 (C-3).

b: 5-Hexen-1,2-diol (2.24 mL, 2.2 g, 18.9 mmol) was added slowly, with stirring, over 10 min to a solution of NaIO$_4$ (4.1 g) in water (45 mL) under ice cooling, and then left at room temperature for 2 h. Ethanol (30 ml) was added and the mixture was filtered to remove precipitated sodium salts, and concentrated. Chloroform (50 ml) and H$_2$O (20 ml) were added, and the organic layer was separated, dried, filtered, and evaporated to dryness. The residue was chromatographed on silica gel (96:4 CHCl$_3$/MeOH) to give 4-penten-1-al (13) as a colorless liquid (1.2 g, 14.2 mmol, 75%).

The spectral properties of the compound were identical with that of the product obtained by method a.

6-Hepten-1-al (18)

This product was prepared from 6-hepten-1-ol (17) (1.9 g, 17 mmol), as described for 5-hexen-1-al (8), Method C. The total yield of the desired (18) was 90%, (15.3 mmol, 1.72 g).

$^1$H NMR: 9.62 (s, 1 H, H-1), 5.83 (m, 1 H, H-6), 4.92 (m, 2 H, H-7), 2.41 (t, 2 H, J = 7.1 Hz, H-2), 1.74 (m, 2 H, H-3), 1.51 (m, 2 H, H-5), 1.35 (m, 6 H, H-4).

$^{13}$C NMR: 202.51 (C-1), 138.04 (C-6), 114.67 (C-7), 43.44 (C-2), 33.43 (C-5), 28.13 (C-3), 24.81 (C-4).

8-Nonen-1-al (22)

This product was prepared from 8-nonen-1-ol[18](21) (2.4 g, 17 mmol) as desribed for 5-hexen-1-al (8), Method C. The residue was subjected to a column chromatography on silica gel (98:2 CHCl3/MeOH), yielding 2.12 g as a syrup (15.13 mmol, 89%) of (22).

$^1$H NMR: 9.65 (s, 1 H, H-1), 5.72 (m, 1 H, H-8), 4.95 (m, 2 H, H-9), 2.43 (t, 2 H, J = 5 Hz, H-2), 2.12 (m, 2 H, H-7), 1.54 (m, 2 H, H-3), 1.33 (m, 6 H, H-4, H-5, H-6).

$^{13}$C NMR: 200.54 (C-1), 138.82 (C-8), 114.11 (C-9), 35.01 (C-2), 34.24 (C-7), 28.83 (C-3), 28.74 (C-6), 23.92 (C-4), 23.24 (C-5).

3-(Allyloxy)propionaldehyde (25)

A solution of allyl alcohol (30 mL, 25.6 g, 0.44 mol), monochloroacetic acid (3 g, 0.032 mol), and sodium hydroxide (1.27 g, 0.032 mol) in H$_2$) (5 mL) was added dropwise, with stirring over 10 min to acrolein (80 mL, 1.2 mol) contained in a 250 ml flask. Acetic acid (12 mL, 0.21 mol) was added and the reaction mixture was maintained at 40° C. for 40 h. After cooling to room temperature, the mixture was washed with H$_2$O (50 mL 33 3), and the organic layer was dried over anhydrous Na$_2$SO$_4$. The solution was concentrated under aspirator vacuum at 40° C. to remove volatile by-products. The residual viscous oil was purified by column chromatography on silica gel using CH$_2$Cl$_2$as a eluent to give 34.2 g of (25) (0.3 mol) as a colorless oil. Yield, 69%.

$^1$H NMR: 9.82 (t, 1 H, J = 1 Hz, H-1), 5.82 (m, 1 H, H-2'), 5.21 (m, 2 H, H-3'), 3.93 (dt, 2 H, J = 3,1 Hz, H-1'), 3.82 (t, 2 H, J = 4 Hz, H-3), 2.61 (dt, 2 H, J = 4, 1 Hz, H-2).

$^{13}$C NMR: 202.12 (C-1), 134.24 (C-2'), 116.24 (C-3'), 71.43 (C-1'), 64.34 (C-3), 34.12 (C-2).

5-Hexen-1,1-diacetate (9)

5-Hexen-1-al (8) (5 g, 5.9 mL, 50.9 mmol) was added dropwise, with stirring over 5 min at ambient temperature to a solution of acetio anhydride (3 mL, 31 mmol) and BF$_3$.Et$_2$O (0.5 mL) in anhydrous Et$_2$O (10 mL). The reaction mixture was stirred for 10 min, then washed successively with 25% NaOAc solution (20 mL) and H$_2$O (25 mL ×2), and dried over anhydrous Na$_2$SO$_4$. The ether was evaporated and the residue was distilled to give the diacetoxy acetal (9) (9.6 g, 48 mmol, 94%). The product was used in subsequent reactions without further purification.

$^1$H NMR: 6.83 (t, 1 H, J = 5 Hz, H-1), 5.58 (m, 1 H, H-5), 5.02 (m, 2 H, H-6), 2.12 (s, 6 H, CH$_3$), 2.05 (m, 2 H, H-2), 1.85 (m, 2 H, H-4), 1.50 (m, 2 H, H-3).

$^{13}$C NMR: 168.42 (COCH3), 137.43 (C-5), 114.81 (C-6), 89.92 (C-1), 32.82 (C-2), 32.14 (C-4), 22.23 (C-3), 20.32 (CH$_3$).

4-Penten-1,1diacetate (14)

The compound was prepared from 4-penten-1-al (13) (6.7 g, 7.8 mL, 80 mmol), acetic anhydride (5.7 mL, 6.13 g, 60 mmol) and BF$_3$.Et$_2$O (0.2 mL) in Et$_2$O (6 mL) as described for (9). After removing the excess of acetic anhydride by distillation, the residue was subjected to a column chromatography on silica gel (97:3 CHCl$_3$/MeOH) to give the diacetoxy acetal (14) (14 g, 75.2 mmol, 94%)

$^1$H NMR: 6.85 (t, 1 H, H-1, J =5 Hz), 5.74 (m, 1 H, H-4), 4.95 (m, 2 H, H-5), 2.05 (m, 2 H, H-2), 2.03 (s, 6 H, CH$_{3ac}$), 1.85 (m, 2 H, H-3).

$^{13}$C NMR: 168.75 (COCH3), 137.64 (C-4), 115.01 (C-5), 89.85 (C-1), 32.96 (C-2), 32.17 (C-3), 20.24 (CH$_3$)

6-Hepten-1,1-diacetate (19)

The compound was prepared from 6-heptenal (18) (4 g, 4.7 mL, 35 mmol), acetic anhydride (2.8 mL, 3.1 g, 30 mmol) and BF$_3$.Et$_2$O (0.2 mL) in EtzO (5 mL) as described for (9). After removing the excess of acetic anhydride by distillation, the residue was subjected to a column chromatography on silica gel (97:3 CHCl$_3$/MeOH) to give the diacetoxy acetal (19) (7.14g, 33.3 mmol, 95%)

$^1$H NMR: 6.87 (t, J =5 Hz, 1 H, H-1), 5.83 (m, 1 H, H-6), 4.98 (m, 2 H, H-7), 2.15 (dt, J =5, 1 Hz, 3 H, H-2), 2.02 (s, 6 H, CH$_{3ac}$,) 1.90 (m, 2 H, H-5), 1.64 (m, 4 H, H-3, H-4).

$^{13}$C NMR: 168.54 (COCH3), 137.93 (C-6), 114.92 (C-7), 89.86 (C-1), 33.43 (C-2), 33.14 (C-5), 24.52 (C-3), 21.21 (C-4), 20.22 (CH$_3$).

2,2-Dimethyl-4-pentene-1,1-diacetate (29)

The compound was prepared from 2,2-dimethyl-4-penten-1-al (28) (3 mL, 2.5 g, 22 mmol) acetic anhydride (1.4 mL, 1.56 g, 15 mmol) and BF$_3$.Et$_2$O (0.2 mL) in Et$_2$O (5 mL) as described for (9) After removing the excess of acetic anhydride by distillation, the residue was subjected to a column chromatography on silica gel (96:4 CHCl$_3$/MeOH) to give the diacetoxy acetal (29) (4.44 g, 20.7 mmol, 94%).

$^1$H NMR: 6.52 (s, 1 H, H-1), 5.75 (m, 1 H, H-4), 4.95 (m, 2 H, H-5), 2.05 (s, 6 H, CH$_{3ac}$), 2.02 (m, 2 H, H-3), 1.85 (s, 6 H, CH$_3$) $^{13}$C NMR: 168.63 (COCH3), 133.46 (C-4), 117.65 (C-5), 93.55 (C-1), 41.43 (C-3), 37.42 (C-2), 21.01 (CH$_3$), 20.34 (CH$_{3ac}$)

8-Nonen-1,1-diacetate (23)

The compound was prepared from 8-nonen-1-al (22) (8.3 mL, 7 g, 50 mmol), acetic anhydride (3.8 mL, 4 g, 40 mmol) and BF$_3$.Et$_2$O (0.2 mL) in Et$_2$O (7 mL) as described for (9). After removing the excess of acetic anhydride by distillation, the residue was subjected to a column chromatography on silica gel (97:3 CHCl$_3$/MeOH) to give the diacetoxy acetal (23) (11.75 g, 48.5 mmol, 97%). $^1$H NMR: 6.82 (t, 1 H, J =5.6 Hz, H-1), 5.75 (m, 1 H, H-8), 4.95 (m, 2 H, H-9), 2.02 (s, 6 H, CH$_{3ac}$), 1.98 (m, 2 H, H-7), 1.75 (m, 2 H, H-2), 1.54 (m, 2 H, H-4), 1.35 (m, 6 H, H-6, H-5, H-3).

$^{13}$C NMR: 168.84 (COCH3), 138.83 (C-8), 114.12 (C-9), 90.43 (C-1), 34.92 (C-2), 34.15 (C-7), 28.84 (C-3), 28.71 (C-6), 23.84 (C-4), 23.21 (C-5), 20.64 (CH$_3$).

3-(Allyloxy)propane-1,1-diacetate (26)

The compound was prepared from 3-(allyloxy)propionaldehyde (25) (5.2 mL, 5 g, 44 mmol), acetic anhydride (2.4 mL, 25 mmol) and BF$_3$/Et$_2$O (0.2 mL) in Et$_2$O (5 mL) as described for (9). After removing the excess of acetic anhydride by distillation, the residue was subjected to a column chromatography on silica gel (96:4 CHCl$_3$/MeOH) to give the diacetoxy acetal(26) (8.94 g, 41.4 mmol, 94%).

$^1$H NMR 6.92 (t, 1 H, J =4 Hz, H-1), 5.85 (m, 1 H, H-2), 5.23 (m, 2 H, H-3), 3.95 (dt, 2 H, J =3,1 Hz, H-1'), 3.44 (t, 2 H, J =4 Hz, H-3), 2.01 (s, 6 H, CH$_{3ac}$), 1.95 (dt, 2 H, J =4, 2 Hz, H-2).

$^{13}$C NMR: 168.02 (COCH3), 134.44 (C-2'), 116.43 (C-3'), 88.42 (C-1), 71.41 (C-1'), 64.76 (C-3), 33.25 (C-2), 20.26 (CH$_3$).

2-Propene-1,1-diacetate (31)

The compound was prepared from acrolein (6 mL, 5 g, 90 mmol), acetic anhydride (5.7 mL, 6.13 g, 60 mmol) and BF$_3$/Et$_2$O (0.25 mL) in Et$_2$O (5 mL) as described for (9) After removing the excess of acetic anhydride by distillation, the residue was subjected to a column chromatography on silica gel (97:3 CHCl$_3$/MeOH) to give the diacetoxy acetal (31) (13.7 g, 86.4 mmol, 96%).

$^1$H NMR: 71.14 (d, J =7 Hz, 1 HJ, H-1), 5.85 (m, 1H, H-2), 5.45 (m, 2 H, H-3), 2.05 (s, 6 H, CH$_3$).

$^{13}$C NMR: 168.15 (COCH3), 131.12 (C-2), 119.44 (C-3), 88.87 (C-1), 20.38 (CH$_3$).

5-Pentanal-1,1-diacetate (10)

A solution of 5-hexen-1,1-diacetate (9) (5 g, 3.5 ml,25 mmol) in CH$_2$Cl$_2$ (5 mL) was placed in a long cylindrical gas absorption vessel with an inlet dispersion tube extending to the base. The vessal was cooled to −70° C. in a dry ice/acetone mixture, and ozone was introduced. Ozonization was continued until all of the compound had reacted (blue color due to the formation of the ozonide), approximately 20 min. Methyl sulfide (7.25 mL, 0.1 mol, 4 equivalents) was added to the blue solution of ozonide and the mixture was stirred overnight to reduce the ozonide to the corresponding aldehyde. The excess methyl sulfide was evaporated, and the residue was subjected to a column chromatography on silica gel (CH$_2$Cl$_2$) giving aldehyde (10) (4.29 g, 21.25 mmol, 85%) as a syrup.

$^1$H NMR: 9.83 (t, 1 H, J =1 Hz, H-5), 6.75 (t, 1 H, J =5 Hz, H-1), 2.66 (dt, 2 H, J =5.5, 1 Hz, H-4), 2.14 (s, 6 H, CH$_3$), 2.05 (m, 2 H, H-2), 1.85 (m, 2 H, H-3).

$^{13}$C NMR: 201.43 (C-5), 168.72 (COCH3), 89.61 (C-1), 42.86 (C-4), 32.10 (C-2), 20.54 (CH$_3$), 15.62 (C-3).

analysis: calc'd for C$_9$H$_{14}$O$_5$ —c, 53.46; H 6.98.
Found - - - - - - - c, 53.61; H 7.87.

4-Butanal-1,1-diacetate (15)

The compound was prepared from 4-penten-1,1-diacetate (14) (4.65 g, 3.45 mL, 25 mmol) in CH$_2$Cl$_2$ (5 mL) as described for (10). After removing the excess of methyl sulfide by distillation, the residue was subjected to a column chromatography on silica gel (CH$_2$Cl$_2$) to give the desired aldehyde (15) (4.04g, 21.5 mmol, 86%) as a colorless oil.

$^1$H NMR: 9.83 (t, 1 H, J =1 Hz, H-4), 6.75 (t, 1 H, J =5 Hz, H-1), 2.66(dt, 2 H, J =5.5, 1 Hz, H-3), 2.14 (s, 6 H, CH3), 2.05 (m, 2 H, H-2).

$^{13}$C NMR: 201.43 (C-4), 168.72 (COCH3), 89.61 (C-1), 42.86 (C-3), 32.10 (C-2), 20.54 (CH$_3$).

6-Hexanal-1,1-diacetate (20)

The compound was prepared from 6-hepten-1,1-diacetate (19) (5.35 g, 3.5 mL, 25 mmol) in $CH_2Cl_2$ (5 mL) as described for (10). After removing the excess of Methyl sulfide by distillation, the residue was subjected to a column chromatography on silica gel ($CH_2Cl_2$) to give the desired aldehyde (20) (4.71g 21.8 mmol, 87%) as a colorless oil.

$^1H$ NMR 9.83 (t, 1 H, J = 1 Hz, H-6), 6.75 (t, 1 H, J =5 Hz, H-1), 2.66 (dt, 2 H, J =5.5, 1 Hz, H-5), 2.14 (s, 6 H, $CH_3$), 2.05 (m, 2 H, H-2), 1.85 (m, 2 H, H-3), 1.82 (m, 2H, H-4).

$^{13}C$ NMR: 201.43 (C-6), 168.72 ($COCH_3$), 89.61 (C-1), 42.86 (C-5), 32.10 (C-2), 20.54 ($CH_3$), 15.62 (C-3), 15.60 (C-4).

8-Octanal-1,1-diacetate (24)

The compound was prepared from 8-nonen-1,1-diacetate (23) (6.05 g, 25 mmol) in $CH_2Cl_2$(5 mL) as described for (10). After removing the excess of Methyl sulfide by distillation, the residue was subjected to a column chromatography on silica gel ($CH_2Cl_2$) to give the desired aldehyde (24) (5.12g, 21 mmol, 84%) as a colorless oil.

$^1H$ NMR: 9.83 (t, 1 H, J = 1 Hz, H-8), 6.75 (t, 1 H, J =5 Hz, H-1), 2.66(dt, 2 H, J =5.5, 1 Hz, H-7), 2.14 (s, 6 H, $CH_3$), 2.05 (m, 2 H, H-2), 1.85 (m, 2 H, H-3), 1.82–1.75 (m, 6H, H-4, H-5, H-6).

$^{13}C$ NMR: 201.50 (C-8), 168.70 ($COCH_3$), 89.66 (C-1), 42.88 (C-7), 32.15 (C-2), 20.58 ($CH_3$), 15.62 (*C-3), 15.60 (*C-4), 15.46 (*C-5), 15.00 (*C-6).

* Assignments for $C_3$, $C_4$, $C_5$ and $C_6$ may be interchanged.

O-(3,3-diacetoxypropyl)glycoladehyde (27)

The compound was prepared from 3-(allyloxy)propane-1,1-diacetate (26) (5.4 g, 25 mmol) in $CH_2Cl_2$ (5 mL) as described for (10). After removing the excess of Methyl sulfide by distillation, the residue was subjected to a column chromatography on silica gel ($CH_2Cl_2$) to give the desired aldehyde (27) (4.58 g, 21 mmol, 84%) as a colorless oil.

$^1H$ NMR: 9.63 (t, 1 H, J = 1 Hz, H-1 ), 6.74 (t, 1 H, J =4.2 Hz, H-1), 4.27 (d, 2 H, J = 1 Hz, H-2'), 3.45 (t, 2 H, J =4.2 Hz, H-3), 2.01 (s, 6 H,$\underline{CH_{3ar}}$), 1.95 (dt, 2 H, J =4, 2 Hz, H-2).

$^{13}C$ NMR: 199.94 (C-1'), 168.35 ($COCH_3$), 88.37 (-1), 72.32 (C-2'), 64.66 (C-3), 33.35 (C-2), 20.36 ($CH_3$).

Analysis Calc'd for $C_9H_{14}O_6$: C,49.54; H, 6.47.
Found: C,49.51; H, 6.58.

2,.2-Dimethyl-4-butanal-1,1-diacetate (30)

The compound was prepared from 2,2-dimethyl-4-pentene-1,1-diacetate (29) (5.32 g, 3.54 mL, 25 mmol) in $CH_2Cl_2$ (5 mL) as described for (10). After removing the excess of Methyl sulfide by distillation, the residue was subjected to a column chromatography on silica gel ($CH_2Cl_2$) to give the desired aldehyde (30) (4.68 g, 21.8 mmol, 87%) as a colorless oil.

$^1H$ NMR: 9.85 (t, 1 H, J = 1 Hz, H-4), 6.65 (t, 1 H, J =5 Hz, H-1), 2.08 (s, 6 H, $CH_{3ac}$), 2.01 (m, 2 H, H-3), 1.85 (s, 6 H, $CH_3$).

$^{13}C$ NMR: 201.05 (C-4), 168.72 ($COCH_3$), 89.65 (C-1), 42.80 (C-3), 37.42 (C-2), 21.50 ($CH_3$), 20.35 ($CH_{3ac}$).

Analysis Calc'd. for $C_{10}H_{16}O_5$: C, 55.55; H, 7.46.
Found: C, 54.67; H, 7.55.

O-(2,2-diacetoxyethyl)glycolaldehyde (35)

This compound was prepared in four steps from anhydrous glycerol by monoalkylation, oxidation of the diol, acetylation and ozonolysis

3-Allyloxy-1,2-propandiol (32)

KOH (11.2 g, 200 mmol) was added cautiously to anhydrous glycerol (60 mL, 821 mmol) in a 250 mL flask, and the mixture was heated to 60° C. under a nitrogen atmosphere until the KOH had dissolved. After cooling to room temperature, allyl bromide (17.3 mL, 20 mmol) was added over 15 min, dropwise with stirring and the mixture was stirred at 90° C. for 14 h. After cooling to room temperature, the mixture was diluted with aqueous 50% $K_2CO_3$ (100 mL) then extracted with $CH_2Cl_2$ (3 ×100 mL). The combined extracts were dried, filtered and evaporated. The residual diol, a colorless oil, 22.5 g (32) (170 mmol, 85%), was used for subsequent reaction without further purification.

$^1H$ NMR: 5.92 (m, 1 H, H-2'), 5.21 (m, 2 H, H-3'), 4.14 (m, 1 H, H-2), 3.97 (m, 2 H, H-3), 3.79 (m, 2 H, H-1'), 3.71 (m, 2 H, H-1).

$^{13}C$ NMR: 134.19 (C-2'), 117.18 (C-3') 72.09 (C-1'), 71.11 (C-1), 70.74 (C-2), 63.72 (C-3).

2-Allyloxyethan-1-al (33)

This diol (32) (1.71 mL, 2.5 g, 18.9 mmol) was added slowly, with stirring, over 10 min to a solution of $NaIO_4$ (4.1 g) in water (45 mL) under ice cooling and then left at room temperature for 2 h. Ethanol (30 ml) was added and the mixture was filtered to remove precipitated sodium salts, and concentrated. Chloroform (50 ml) and $H_2O$ (20 ml) were added, and the organic layer was separated, dried, filtered, and evaporated to dryness. The residue was chromatographed on silica gel (96:4 $CHCl_3$/MeOH) to give allyloxy glycol aldehyde (33) as a colorless liquid (1.32 g, 13.2 mmol, 70%).

$^1H$ NMR: 9.73 (t, 1 H, J = 1 Hz, H-1), 5.95 (m, 1 H, h-2'), 5.37 (m, 2 H, H-3'), 4.05 (m, 4 H, H-1, H-2).

$^{13}C$ NMR: 199.86 (C-1), 133.32 (C-2'), 117.02 (C-3'), 74.65 (C-2), 71.64 (C-1').

2-Allyloxyethane-1,1-diacetate (34)

The aldehyde (33) (1.32 g, 13.2 mmol) was added dropwise, with stirring, over 5 min at ambient temperature to a solution of acetic anhydride (1.5 mL, 16.5 mmol), $Et_2O$ (5 mL) and $BF_3.Et_2O$ (0.1 mL). The reaction mixture was stirred for 10 min then washed sucessively with 25% NaOAc solution (5 mL) and $H_2O$ (10 mL 33 2), and dried over anhydrous $Na_2SO_4$. After removing the excess of acetic anhydride by distillation, the residue was subjected to a column chromatography on silica gel (97:3 $CHCl_3$/MeOH) to give the diacetoxyacetal(34) (2.55 g, 12.6 mmol, 95%).

$^1H$ NMR: 6.82 (t, 1 H, J =5 Hz, H-1), 5.75 (m, 1 H, H-2'), 5.15 (m, 2 H, H-3'), 3.98 (m, 2 H, H-1'), 3.55 (d, 2 H, J =5 Hz, H-2), 2.09 (s, 6 H, $CH_3$).

$^{13}C$ NMR: 168.33 ($COCH_3$) 133.74 (C-2'), 117.21 (C-3'), 87.34 (C-1), 72.04 (C-1', 68.53 (C-2), 20.31 ($CH_3$).

O-(2,2-diacetoxyethyl)glycolaldehyde (35)

The diacetoxy acetal (34) (2.55 g, 12.6 mmol) in $CH_2Cl_2$ (5 mL) was ozonized as described for compound (10). Methyl sulfide (3.7 mL, 50.5 mmol, 4 equiv.) was added to the blue ozonide sulution and the mixture was stirred overnight. Evaporation of solvent and unreacted methyl sulfide, and chromatography on silica gel ($CH_2Cl_2$ eluent) gave the corresponding aldehyde (35), (2.21 g, 10.84 mmol, 86%).

$^1$H NMR: 9.62 (t, 1 H, J = 1 Hz, H-1'), 6.84 (t, 1 H, J = 5.2 Hz, H-1), 4.23 (d, 2 H, J = 1 Hz, H-2'), 3.86 (d, 2 H, J = 5.2 Hz, H-2), 2.01 (s, 6 H, CH$_3$)

$^{13}$C NMR: 199.94 (C-1'), 168.35 (COCH$_3$), 87.37 (C-1), 72.32 (C-2'), 68.51 (C-2), 20.35 (CH$_3$).

Analysis calc'd. for C$_8$H$_{12}$O$_6$: C, 47.06; H, 5.92.
Found: C, 46.84; H, 5.81.

Ethyl allyl-4-butyrate (16)

A solution of heptenoic acid (1.1 mL, 1 g, 7.8 mmol) in ethanol (2 mL) was added to a stirred solution of p-toluene sulfonic acid (0.19 g, 1 mmol) in ethanol (10 mL). The mixture was stirred at 60° C. for 2 h, then allowed to cool to room temperature. Aqueous NaHCO$_3$ (50%) was added (25 mL), and the organic layer was extracted with CHhdCl$_2$ (2 ×25 mL), dried over Na$_2$SO$_4$, filtered and evaporated. The colorless oil which remained was identified as the desired ester (16), (1.19 g, 7.64 mmol, 98%).

$^1$H NMR: 5.83 (m, 1 H, H-6), 4.96 (m, 2 H, H-7), 4.15 (q, 2 H, q, J = 7 Hz, OCH$_2$CH$_3$), 2.36 (t, J = 7.2 Hz, 2 H, H-2), 2.05 (q, J = 8 Hz, 2 H, H-5), 1.61 (m, 2 H, H-3), 1.45 (m, 2 H, H-4), 1.33 (t, 3 H, J = 7 Hz, OCH$_2$CH$_3$).
$^{13}$C NMR: 173.34 (C-1), 138.01 (C-6), 114.32 (C-7), 58.83 (OCH$_2$CH$_3$), 33.82 (C-2), 33.01 (C-5), 28.02 (C-3), 24.14 (C-4), 13.72 (OCH$_2$CH$_3$).

6-Hepten-1-ol (17)

A solution of the ester (16), (0.6 g, 3.85 mmol) in THF (5 mL) was cooled to 0° C. in an ice/salt bath. A solution of DIBAL (1 M in Hexane, 6 mL, 6 mmol) was added dropwise with stirring over 10 min. The solution was then warmed to ambient temperature and allowed to stir for an additional 2 h. The excess DIBAL was carefully quenched by the addition of 10 mL of H$_2$O. The organic layer was extracted with CHCl$_3$ (2 ×15 mL), combined, and dried over Na$_2$SO$_4$. Evaporation of the solvent, chromatography on silica gel (93:7 CHCl$_3$/MeOH) gave the alcohol (17) as a colorless oil (0.4 g, 3.54 mmol, 92%).

$^1$H NMR: 5.85 (m, 1 H, H-6), 4.95 (m, 2 H, H-7), 3.62 (t, 2 H, J = 6 Hz, H-1), 2.62 (bs, 1 H, OH), 2.02 (m, 2 H, H-2), 1.54 (m, 2 H, H-5), 1.55 (m, 4 H, H-3, H-4.

$^{13}$C NMR: 138.76 (C-6), 114.24 (C-7), 62.5 (C-1), 33.62 (C-2), 32.47 (C-5), 28.60 (*C-3), 25.11 (*C-4).
* Assignments for C$_3$ and C$_4$ may be interchanged.

N-(5,5-Diacetoxypentyl) dioxorubicin hydrochloride (2a)

A stirred solution of doxorubicin hydrochloride (20 mg, 0.035 mmol) and 5-pentanal-1,1-diacetate (10) (14 mg, 2 eq, 0.07 mmol) in CH$_3$CN-H$_2$O (2:1) (5 mL) was treated with a solution of NaBH$_3$CN (1M in THF) (24 uL, 0.67 eq, 0.024 mmol). The mixture was stirred under a nitrogen atmosphere at room temperature in the dark for 1 h. When reaction was complete (as evidenced by TLC of a 5 uL aliquot) the solution was diluted with H$_2$O (8 ml) and then extracted repeatedly (10 ×10 mL) with CHCl$_3$-MeOH (5:1). The combined extracts were dried and evaporated to give a red amorphous solid (16 mg). Preparative TLC of this product (,CHCl$_3$-MeOH, 10:1; R$_f$ 32 0.60) afforded N-(pentan-5-al diacetoxy acetal) doxorubicin (10 mg, 0.0137 mmol). The product was suspended in H$_2$O (1 mL) and acidified to pH 5 by dropwise addition of 0.05 N HCl (approx. 0.5 mL). The solution was lyophilized to afford the title compound (10.25 mg ,0.0134 mmol, 38%). It was then stored under a nitrogen atmosphere in a tightly stoppered vessel at −78° C. in the dark.

$^1$H NMR (free base) : 8.01 (dd, J = 8.2, 0.9 Hz, 1 H, H-1), 7.82 (t, J = 8.2 Hz, 1 H, H-2), 7.39 (dd, J = 8.2, 0.9 Hz, 1 H, H-3), 6.73 (t, J = 5.46, 1 H, H-5''), 5.52 (t, J 32 1 Hz, 1 H, H-1'), 5.3 (bs, 1 H, H-7), 4.75 (s, 2 H, H-14), 4.12 (s, 3 H, CH$_{3ar.}$), 3.62 (bs, 1 H, H-5'), 3.62 (m, 1 H, H-4'), 3.25 (d, J = 16 Hz, 1 H, H-10a), 2.95 (d, J = 16 Hz, 1 H, H-10b), 2.85 (m, 1 H, H-3'), 2.65 (m, 2 H, H-1''), 2.35 (m, 1 H, H-8a), 2.25 (m, 1 H, H-8b), 2.01 (s, 6 H, CH$_{3ac.}$), 1.82 (m, 2 H, H-2'a), 1.76 (m, 2 H, H-4''), 1.75 (m, 1 H, H-2'b), 1.40 (m, 2 H, H-3''), 1.35 (d, J = 6 Hz, 3 H, H-6').

MS (electrospray): 730 (M +H)$^+$.

N-(2,2-Diacetoxyethyloxyethyl) doxorubicin HCl (2b)

The compound was prepared from doxorubicin HCl (20 mg, 0.035 mmol, O-(2,2-diacetoxyethyl)glycolaldehyde (35) (14.3 mg, 2 eq., 0.07 mmol), NaBH$_3$CN (1 M in THF) (24 ul, 0.67 eq, 0.024 mmol) in CH$_3$CN-H$_2$O (2:1) (5 mL), as desribed for (2a). When reaction was complete (as evidenced by TLC of a 5 uL aliquot) the solution was diluted with H$_2$O (8 ml) and then extracted repeatedly (10 ×10 mL) with CHCl$_3$-MeOH (5:1). The combined extracts were dried and evaporated to give a red amorphous solid (17.5 mg). Preparative TLC of this product (CHCl$_3$-MeOH, 10:1; R$_f$=0.6) afforded N-(2,2-diacetoxyethyloxyethyl) doxorubicin (9.1 mg, 0.012 mmol). The product was suspended in H$_2$O (1mL) and acidified to pH 5 by dropwise addition of 0.05 N HCl (approx. 0.5 mL). The solution was lyophilized to afford the title compound (9.4 mg, 0.012 mmol, 34%). It was then stored under a nitrogen atmosphere in a tightly stoppered vessel at −78° C. in the dark.

MS- electrospray : 746 (M +Me +1).

$^1$H NMR (free base) : 8.11 (dd, J = 8.2, 0.8 Hz, 1 H, H-1), 7.82 (t, J = 8.2 Hz, 1 H, H-2), 7.35 (dd, J = 8.2, 0.8 Hz, 1 H, H-3), 6.75 (t, 1 H, J = 5.5, H-1b'') 5.50 (t, J = 1 Hz, 1 H, H-1'), 5.35 (bs, 1 H, H-7), 4.75 (s, 2 H, H-14), 4.11 (s, 3 H, CH$_{3ar.}$), 3.84 (bs, 1 H, H-5'), 3.77 (m, 1 H, H-4'), 3.65 (m, 2 H, H-2''a), 3.54 (m, 2 H, H-2b''), 3.25 (d, J = 16 Hz, 1 H, H-10a), 3.21 (m, 1 H, H-3'), 3.14 (m, 2 H, H-1''), 2.95 (d, J = 16 Hz, 1 H, H-10b), 2.35 (m, 1 H, H-8a), 2.25 (m, 1 H, H-8b), 2.24 (m, 2 H, H-2'a), 2.12 (m, 1 H, H-2'b), 2.01 (s, 6 H, CH$_{3ac.}$), 1.34 (d, J = 6 Hz, 3 H, H-6').

N-(4,4-Diacetoxybutyl) doxorubicin HCl (2c):

The compound was prepared from doxorubicin. HCl (20 mg, 0.035 mmol), 4-butanal-1,1-diacetate (15) (13.2 mg, 2 eq., 0.07 mmol) and NaBH$_3$CN (1 M in THF) (24 ul, 0.67 eq., 0.024 mmol) in CH$_2$CN-H$_2$O (2:1) (5 mL) as described for (2a). When reaction was complete (as evidenced by TLC of a 5 uL aliquot) the solution was diluted with H$_2$O (8 ml) and then extracted repeatedly (9 ×10 mL) with CHCl$_3$-MeOH (5:1). The combined extracts were dried and evaporated to give a red amorphous solid (15 mg). Preparative TLC of this product (CHCl$_3$-MeOH, 10:1; R$_f$=0.59) afforded (4,4-diacetoxybutyl) doxorubicin (10 mg, 0.014 mmol). The product was suspended in H$_2$O (1 mL) and acidified to pH 5 by dropwise addition of 0.05 N HCl (approx. 0.5 mL). The solution was lyophilized to afford the title compound (10.17 mg ,0.0135 mmol, 39%). It was then stored under a nitrogen atmosphere in a tightly stoppered vessel at −78° C in the dark.

$^1$H NMR (free base) : 8.05 (dd, J = 8.1, 0.85 Hz, 1 H, H-1), 7.90 (t, J = 8.1 Hz, 1 H, H-2), 7.42 (dd, J = 8.1, 0.85 Hz, 1 H, H-3), 6.75 (t, J =5.45 Hz, 1 H, H-4″), 5.52 (bs, 1 H, H-1′), 5.31 (bs, 1 H, H-7), 4.72 (s, 2 H, H-14), 4.05 (s, 3 H, CH$_{3ar.}$), 3.65 (bs, 1 H, H-5′), 3.61 (m, 1 H, H-4′), 3.32 (d, J =16.2 Hz, 1 H, H-10a), 3.03 (d, J =16.2 Hz, 1 H, H-10b), 2.81 (m, 1 H, H-3′), 2.60 (m, 2 H, H-1″), 2.44 (m, 1 H, H-8a), 2.22 (m, 1 H, H-8b), 2.02 (s, 6 H, CH$_{3ac.}$), 1.75 (m, 2 H, H-2′a), 1.75 (m, 2 H, H-3″), 1.71 (m, 2 H, H-2′b), 1.42 (m, 2 H, H-2″), 1.35 (d, J =6 Hz, 3 H, H-6′).

N-(6,6-Diacetoxyhexyl) doxorubicin hydrochloride (2d)

A stirred solution of doxorubicin hydrochloride (20 mg, 0.035 mmol) and 6-hexanal-1,1-diacetate (20) (15 mg, 2 eg, 0.07 mmol) in CH$_3$CN-H$_2$O (2:1) (5 mL) was treated with a solution of NaBH$_3$CN (1M in THF) (24 uL, 0.67 eg, 0.024 mmol). The mixture was stirred under a nitrogen atomsphere at room temperature in the dark for 1 hour. When reaction was complete (as evidenced by TLC of a 5 uL aliquot) the solution was diluted with H$_2$O (8 ml) and then extracted repeatedly (10 ×10 mL) with CHCl$_3$-MeOH (5:1). The combined extracts were dried and evaporated to give a red amorphous solid (18 mg). Preparative TLC of this product (CHCl$_3$-MeOH, 10:1; R$_f$ =0.60) afforded N-(6,6-diacetoxyhexyl) doxorubicin (10.4 mg, 0.014 mmol). The product was suspended in H$_2$O (1 mL) and acidified to pH 5 by dropwise additin of 0.05 N HCl (approx. 0.5 mL). The solution was lyophilized to afford the title compound (10.75 mg, 0.0138 mmol, 39%). It was then stored under a nitrogen atmosphere in a tightly stoppered vessel at −78° C. in the dark.

$^1$H NMR (free base) : 8.03 (dd, J =8.2, 0.9 Hz, 1 H, H-1), 7.84 (t, J =8.2 Hz, 1 H, H-2), 7.37 (dd, J =8.2, 0.9 Hz, 1 H, H-3), 6.76 (t, J =5.46, 1 H, H-6″), 5.52 (t, J =1 Hz, 1 H, H-1′), 5.4 (bs, 1 H, H-7), 4.75 (s, 2 H, H-14), 4.14 (s, 3 H, CH$_{3ar.}$), 3.65 (bs, 1 H, H-5′), 3.63 (m, 1 H, H-4′), 3.25 (d, J =16 Hz, 1 H, H-10a), 2.96 (d, J =16 Hz, 1 H, H-10b), 2.85 (m, 1 H, H-3′), 2.66 (m, 2 H, H-1″), 2.36 (m, 1 H, H-8a), 2.23 (m, 1 H, H-8b), 2.05 (s, 6 H, CH$_{3ac.}$), 1.82 (m, 2 H, H02′a), 1.78 (m, 2 H, H-5″), 1.75 (m, 1 H, H-2′b), 1.65 (m, 2 H, H-2″), 1.40 (m, 2 H, H-3″), 1.39 (m, 2 H, H-4″), 1.32 (d, J =6 Hz, 3 H, H-6′).

N-(4,4-Diacetoxy-3,3-dimethylbutyl) doxorubicin HCl (2e)

The compound was prepared from doxorubicin HCl (20 mg, 0.035 mmol), dimethyl 2,2-dimethyl-4-butanal-1,1-diacetate (30) (15 mg, 2 eq., 0.07 mmol) and NaBH$_3$CN (1 M in THF) (24 uL, 0.67 eq., 0.024 mmol), in CH$_3$CN-H$_2$O (2:1) (5 mL), as described for (2a). When reaction was complete (as evidenced by TLC of a 5 uL aliquot) the solution was diluted with H$_2$O (8 ml) and then extracted repeatedly (9 ×10 mL) with CHCL$_3$-MeOH (5:1). The combined extracts were dried and evaporated to give a red amorphous solid (17 mg). Preparative TLC of this product (CHCl$_3$-MeOH, 10:1; R$_f$ =0.54) afforded N-(4,4-diacetoxy-3,3-dimethylbutyl) doxorubicin (11.2 mg, 0.015 mmol). The product was suspended in H$_2$O (1 mL) and acidified to pH 5 by dropwise addition of 0.05 N HCl (approx. 0.5 mL). The solution was lyophilized to afford the title compound (10.8 mg, 0.0138 mmol, 39%). It was then stored under a nitrogen atmosphere in a tightly stoppered vessel at −78° C. in the dark.

$^1$H NMR (free base) : 8.02 (dd, J =8.15, 0.83 Hz, 1 H, H-1), 7.91 (t, J =8.15 Hz, H, H-2), 7.54 (dd, J =8.15, 0.83 Hz, 1 H, H-3), 6.65 (s, 1 H, H-4″), 5.52 (bs, 1 H, H-1′), 5.35 (bs, 1 H, H-7), 4.72 (s, 2 H, H-14), 4.03 (s, 3 H, CH$_{3ar.}$), 3.65 (bs, 1 H, H-5′), 3.60 (m, 1 H, H-4′), 3.35 (d, J =16.4, Hz, 1 H, H-10a), 3.05 (d, J =16.4 Hz, 1 H, H-10b), 2.95 (m, 1 H, H-3′), 2.61 (m, 2 H, H-1″), 2.40 (m, 1 H, H-8a), 2.26 (m, 1 H, H-8b), 2.01 (s, 6 H, CH$_{3ac.}$), 1.78 (m, 2 H, H-2′a), 1.73 (m, 1 H, H-2′b), 1.55 (s, 6 H, CH3), 1.52 (m, 2 H, H-2″), 1.35 (d, J =6 Hz, 3 H, H-6′).

N-(3,3-Diacetoxypropyloxy-1-ethyl) doxorubicin HCl (2f)

The compound was prepared from doxorubicin HCl (20 mg, 0.035 mmol, 3,3-diacetatepropyloxy-1-ethanal (27) (15.2 mg, 2 eq., 0.07 mmol), NaBH$_3$CN (1 M in THF) (24 ul, 0.67 eq, 0.024 mmol) in Ch$_3$CN-H$_2$O (2:1) (5 mL), as desribed for (2a). When reaction was complete (as evidenced by TLC of a 5 uL aliquot) the solution was diluted with H$_2$O (8 ml) and then extracted repeatedly (10 ×10 mL) with CHCl$_3$-MeOH (5:1). The combined extracts were dried and evaporated to give a red amorphous solid (17.5 mg). Preparative TLC of this product (CHCl$_3$-MeOH, 10:1; R$_f$ =0.6) afforded N-(3,3-diacetoxypropyloxyethyl) doxorubicin (9.1 mg, 0.012 mmol). The product was suspended in H$_2$O (1 mL) and acidified to pH 5 by dropwise addition of 0.05 N HCl (approx. 0.5 mL). The solution was lyophilized to afford the title compound (9.4 mg, 0.012 mmol, 34%). It was then stored under a nitrogen atmosphere in a tightly stoppered vessel at −78° C in the dark.

$^1$H NMR (free base) : 8.10 (dd, J =8.1, 0.8 Hz, 1 H, H-1), 7.82 (t, J =8.1Hz, 1 H, H-2), 7.34 (dd, J =8.1, 0.8 Hz, 1 H, H-3), 6.73 (t, J =5.4 Hz, 1 H, H-1″c) 5.52 (t, J =1 Hz, 1 H, H-1′), 5.4 (bs, 1 H, H-7), 4.73 (s, 2 H, H-14), 4.12 (s, 3 H, CH$_{3ar.}$), 3.82 (bs, 1 H, H-5′), 3.75 (m, 1 H, H-4′), 3.62 (m, 2 H, H-2″a), 3.53 (m, 2 H, H-2b″), 3.25 (d, J =16 Hz, 1 H, H-10a), 3.20 (m, 1 H, H-3′), 3.15 (m, 2 H, H-1″a), 2.95 (d, J =16 Hz, 1 H, H-10b), 2.38 (m, 1 H, H-8a), 2.35 (m, 1 H, H-8b), 2.24 (m, 2 H, H-2′a), 2.15 (m, 1 H, H-2′b), 2.02(s, 6 H, CH$_{3ac.}$), 1.95 (dt, 2 H, J =5.4, 2 Hz, H-2″b), 1.35 (d, J =6 Hz, 3 H, H-6′).

N-(8,8-Diacetoxyoctyl) doxorubicin hydrochloride (2g)

A stirred solution of doxorubicin hydrochloride (20 mg, 0.035 mmol) and 8-octanal-1, 1-diacetate (24) (17.1 mg, 2 eg, 0.07 mmol) in CH$_3$CN-H$_2$O (2:1) (5 mL) was treated with a solution of NaBH$_3$CN (1M in THF) (24 uL, 0.67 eg, 0.024 mmol). The mixture was stirred under a nitrogen atmosphere at room termperature in the dark for 1 hour. When reaction was complete (as evidenced by TLC of a 5 uL aliquot) the solution was diluted with H$_2$O (8 ml) and then extracted repeatedly (10 ×10 mL) with CHCl$_3$-MeOH (5:1). The combined extracts were dried and evaporated to give a red amorphous solid (19 mg). Preparative TLC of this product (CHCl$_3$-MeOH, 10:1; R$_f$ =0.60) afforded N-(8,8-diacetoxyoctyl) doxorubicin (11.6 mg, 0.015 mmol). The product was suspended in H$_2$O (1 mL) and acidified to pH 5 by dropwise addition of 0.05 N HCl (approx. 0.5 mL). The solution was lyophilized to afford the title compound (11.72 mg, 0.0145 mmol, 41%). It was then stored under a nitrogen atmosphere in a tightly stoppered vessel at 31 78° C. in the dark.

$^1$h NMR (free base) : 8.05 (dd, J =8.2, 0.9 Hz, 1 H, H-1), 7.85 (t, J =8.2 Hz, 1 H, H-2), 7.40 (dd, J =8.2, 0.9 Hz, 1 H, H-3), 6.72 (t, J =5.46, 1 H, H-8″), 5.55 (T, J =1 Hz, 1 H, H-1′), 5.35 (bs, 1 H, H-7), 4.71 (s, 2 H, H-14), 4.16 (s, 3 H, CH$_{3ar.}$), 3.68 (bs, 1 H, H-5′), 3.65 (m, 1 H, H-4′), 3.28 (d, J =16 Hz, 1 H, H-10a), 2.98 (d, J =16 Hz, 1 H, H-10b), 2.85 (m, 1 H, H-3′), 2.68 (m, 2 H, H-1″), 2.35 (m, 1 H, H-8a), 2.25 (m, 1 H, H-8b), 2.04 (s, 6 H, CH$_{3ac.}$), 1.85 (m, 2 H, H-2'a), 1.75 (m, 2 H, H-741 ), 1.76 (m, 1 H, H-2'b), 1.68 (m, 2 H, H-2''), 1.41 (m, 2 H, H-3—), 1.40 (m, 6 H, H-4'', H-5''), 1.39 (m, 2 H, H-6''), 1.35 (d, J =6 Hz, 3 H, H-6').

By usage of analogous cogeners, those of skill in the art may readily adopt the above synthetic methods to produce almost innumerable varieties of the subject compounds.

The following references as well as those listed in the body of the specification are incorporated in pertinent part herein for the reasons cited.

REFERENCES

1. Young, R. C.; Ozols, R. F.; Myers, C. E. *N. Engl. J. Med.* 1981, 305, 139.
2. Arcamone, F. *Cancer Res.* 1985, 45, 5995.
3. Brown, J. R.; Imam, S. H. *Progr. Med. Chem.* 1984, 21, 169.
4. Muggia F. M.; Young C. W.; Carter S. K. (Eds.) *Anthracycline Antibiotics in Cancer Therapy, Martinus Nijhoff, Publishers,* 1982.
5. Mosher, C. S.; Wu, H. Y.; Fujiwara, A. N.; Acton, E. M. *J. Med. Chem.* 1982, 25, 18.
6. Acton, E. M.; Tong, G. L.; Mosher, C. W.; Wolgemuth, R. L. *J. Med. Chem.* 1984, 27, 638.
7. Acton, M,; Wasserman, K.; Newman R. A. *Anthracyclines and Anthracenedione Based Antitumor Agents: Morpholinyl Anthracyclines;* Lown W. J.; Ed., Elsevier Science Publishers: Amsterdam, In press, 1989.
8. Johnston, J. B.; Habernicht, B.; Acton, E. M.; Glaser, R. I. *Biochem. Pharmacol.* 1983, 32, 3255.
9. Sikic, B. I.; Ehsan, M. N.; Harker, W. G.; Friend, N. F.; Brown, B. W.; Newman, R. A.; Hacker, M. P.; Acton, E. M. *Science,* 1985, 228, 1544.
10. Streeter, D. G.; Taylor, D. L.; Acton, E. M.; Peters, J. H. *Cancer Chemother. Pharmacol.* 1985, 14, 160.
11. Guiliani, F. C.; Barbieri, B.; Geroni, C.; Facchinetti, T.; Casazza, A. M.; Acton, E. M. *Proc. Am. Assoc. Cancer Res.* 1984, 25, 305.
12. Pommier, Y.; Kerrigan, D.; Schwartz, R. E.; Swach, J. A.; McCurdy, A. *Cancer REs.* 1986, 46, 3075.
13. Streeter, D. G.; Johl, J. S.; Gordon, G. R.; Peters, J. H. *Cancer Chemother. Pharmacol.* 1986, 16, 247.
14. (a) Fieser, L. F.; Fieser, M., Ed., In: *Reagents for Organic Synthesis,* Wiley, J. and Sons, 1967, Vol. 1, pp. 142. (b) Bowden, K.; Heilbron, I. M.; Jones, E. R. H.; Weedon, B. C. L; *J. Chem. Soc.* 39 1946, 39.
15. corey, E. J.; Suggs, J. W. *Tetrahedron Lett.,* 1975, 2647.
16. Griffith, W. P.; Ley, S. V.; Whitcombe, G. P.; White, A. D. *J. Chem. Soc. (chem. Commun.),* 1987, 1625.
17. Wang, Y. and Farquhar, D. *J. Med. Chem.* (In press).
18. Alfrebro Inc., 1055 Reed Road, Monroe, OH 45050.

What is claimed is:

1. A compound of the formula

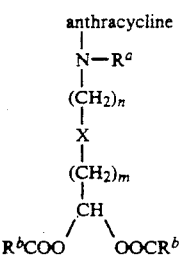

where:
anthracycline is doxorubicin, or daunorubicin;
N is the 3'nitrogen of daunosamine;
$R^a$ is H, methyl, ethyl, propyl or butyl;
X is O, S, $CR^c_2$ or $NR^c$, wherein $R^c$ is H, methyl, ethyl, propyl or butyl;
$R^b$ is methyl, ethyl, porpyl or butyl;
n is 1 to 6; and
m is 0 to 6.

2. The compound of claim 1 wherein $R^a$ is H, $R^b$ is CH$_3$, X is $CR^c_2$, $R^c$ is H, n is 2 and m is 1.
3. The compound of claim 1 wherein $R^a$ is CH$_3$ or H, $R^b$ is CH$_3$, X is O, n is 2, and m is 1.
4. The compound of claim 1 wherein $R^a$ is H, $R^b$ is CH$_3$, X is $CR^c_2$, $R^c$ is H, n is 2 and m is 2.
5. The compound of claim 1 wherein $R^a$ is a H, $R^b$ is CH$_3$, X is $CR^c_2$c, $R^c$ is H, n is 2 and m is 0.
6. The compound of claim 1 wherein $R^a$ is H, $R^b$ is CH$_3$, X is O, n is 2 and m is 2.
7. The compound of claim 1 wherein $R^1$ is H, $R^b$ is CH$_3$, X is $CR^c_2$, $R^c$ is H, n is 2 and m is 4.
8. The compound of claim 1 wherein $R^b$ is methyl.
9. The compound of claim 1 wherein X is $CR^c_2$, $R^c$ is H, and m + n is from 1 to 9.
10. The compound of claim 1 wherein X is O, S or $NR^c$, $R^c$ is H.
11. The compound of claim 1 wherein the anthracycline is doxorubicin.
12. N-(5,5-Diacetoxypentyl doxorubicin or a pharmaceutically acceptable salt thereof.
13. N-(2,2diacetoxyethyloxyethyl) doxorubicin or a pharmaceutically acceptable salt thereof.
14. N-(4,4Diacetoxybutyl) doxorubicin or a pharmaceutically acceptable salt thereof.
15. N-(6,6-Diacetoxyhexyl) doxorubicin or a pharmaceutically acceptable salt thereof.
16. N-(4,4-Diacetoxy-3,3-dimethylbutyl) doxorubicin or a pharmaceutically acceptable salt thereof.
17. N-(3,3-diacetoxypropyloxy-1-ethyl) doxorubicin or a pharmaceutically acceptable salt thereof.
18. N-(8,8-Diacetoxyoctyl) doxorubicin or a pharmaceutically acceptable salt thereof.

* * * * *

UNITED STATES PATENT AND TRADEMARK OFFICE
CERTIFICATE OF CORRECTION

PATENT NO. : 5,196,522          Page 1 of 2
DATED     : March 23, 1993
INVENTOR(S) : FARQUHAR et al It is certified that error appears in the above-indentified patent and that said Letters Patent is hereby corrected as shown below:

In claim 1, column 18, line 21, delete "porpyl" and insert --propyl--, therefor.

In claim 5, column 18, line 30, delete "a" immediately after the first occurrence of 'is'.

In claim 5, column 18, line 31, delete "c" immediately after the subscript '2'.

In claim 7, column 18, line 34, delete the superscript "1" and insert the superscript "a", therefor.

In claim 13, column 18, line 45, delete "N-(2,2diacetoxyethyloxyethyl)" and insert, --N-(2,2-Diacetoxyethyloxyethyl) --. therefor.

In claim 14, column 18, line 47, delete "N-(4,4Diacetoxybutyl)" and insert, --N-(4,4-Diacetoxybutyl)--, therefor.

UNITED STATES PATENT AND TRADEMARK OFFICE
CERTIFICATE OF CORRECTION

PATENT NO. : 5,196,522
DATED : March 23, 1993
INVENTOR(S) : FARQUHAR et al

It is certified that error appears in the above-indentified patent and that said Letters Patent is hereby corrected as shown below:

In claim 17, column 18, line 53, delete "N-(3,3-diacetoxypropyloxy-1-ethyl) and insert, --N-(3,3-Diacetoxypropyloxy-1-ethyl) --. therefor.

Signed and Sealed this

Fourteenth Day of December, 1993

Attest:

BRUCE LEHMAN

*Attesting Officer*  *Commissioner of Patents and Trademarks*